United States Patent
Selig et al.

(10) Patent No.: US 8,613,627 B2
(45) Date of Patent: Dec. 24, 2013

(54) UNIVERSAL CONNECTOR SOCKET

(75) Inventors: Peter Selig, Hechingen (DE); Roland Hundt, Gomaringen (DE)

(73) Assignee: Erbe Elektromedizin GmbH, Tubingen (DE)

( * ) Notice: Subject to any disclaimer, the term of this patent is extended or adjusted under 35 U.S.C. 154(b) by 54 days.

(21) Appl. No.: 13/367,476

(22) Filed: Feb. 7, 2012

(65) Prior Publication Data

US 2012/0202388 A1 Aug. 9, 2012

(30) Foreign Application Priority Data

Feb. 9, 2011 (EP) .................................. 11 153 757

(51) Int. Cl.
*H01R 27/00* (2006.01)
(52) U.S. Cl.
USPC ........................................................ 439/222
(58) Field of Classification Search
USPC ......................................... 439/222, 221, 218
See application file for complete search history.

(56) References Cited

U.S. PATENT DOCUMENTS

| | | | | |
|---|---|---|---|---|
| 5,405,269 A | * | 4/1995 | Stupecky | 439/191 |
| 5,562,503 A | * | 10/1996 | Ellman et al. | 439/638 |
| 5,573,424 A | | 11/1996 | Poppe | |
| 5,679,022 A | * | 10/1997 | Cappa et al. | 439/502 |
| 6,240,315 B1 | * | 5/2001 | Mo et al. | 607/41 |
| 6,402,743 B1 | * | 6/2002 | Orszulak et al. | 606/34 |
| 6,988,423 B2 | * | 1/2006 | Bolam et al. | 73/865.9 |
| 7,094,231 B1 | * | 8/2006 | Ellman et al. | 606/37 |
| 8,177,782 B2 | * | 5/2012 | Beller et al. | 606/34 |
| 2003/0078572 A1 | | 4/2003 | Pearson et al. | |

FOREIGN PATENT DOCUMENTS

DE    10 2009 022363 A1    10/2010

* cited by examiner

*Primary Examiner* — Phuong Dinh
(74) *Attorney, Agent, or Firm* — Dickstein Shapiro LLP

(57) ABSTRACT

A universal connector socket for a surgical apparatus for the connection of different plug connectors of different surgical instruments for RF surgery. The universal connector socket has several plug contact openings for selectively connecting monopolar and bipolar surgical instruments and has several plug contact openings arranged in an overlapping manner for defining an unambiguous plug-in position of a plug connector and a shared reference plug contact opening.

12 Claims, 3 Drawing Sheets

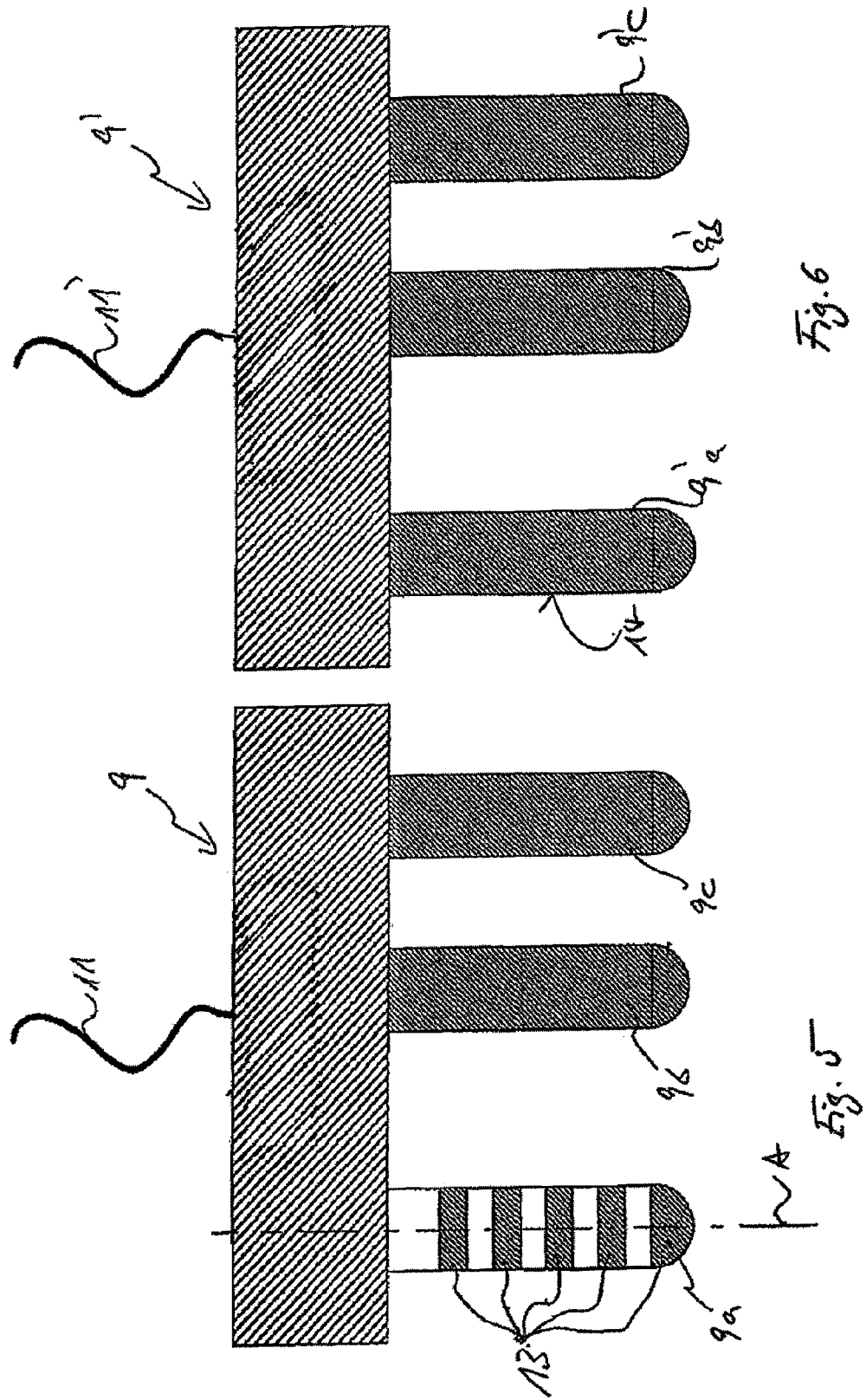

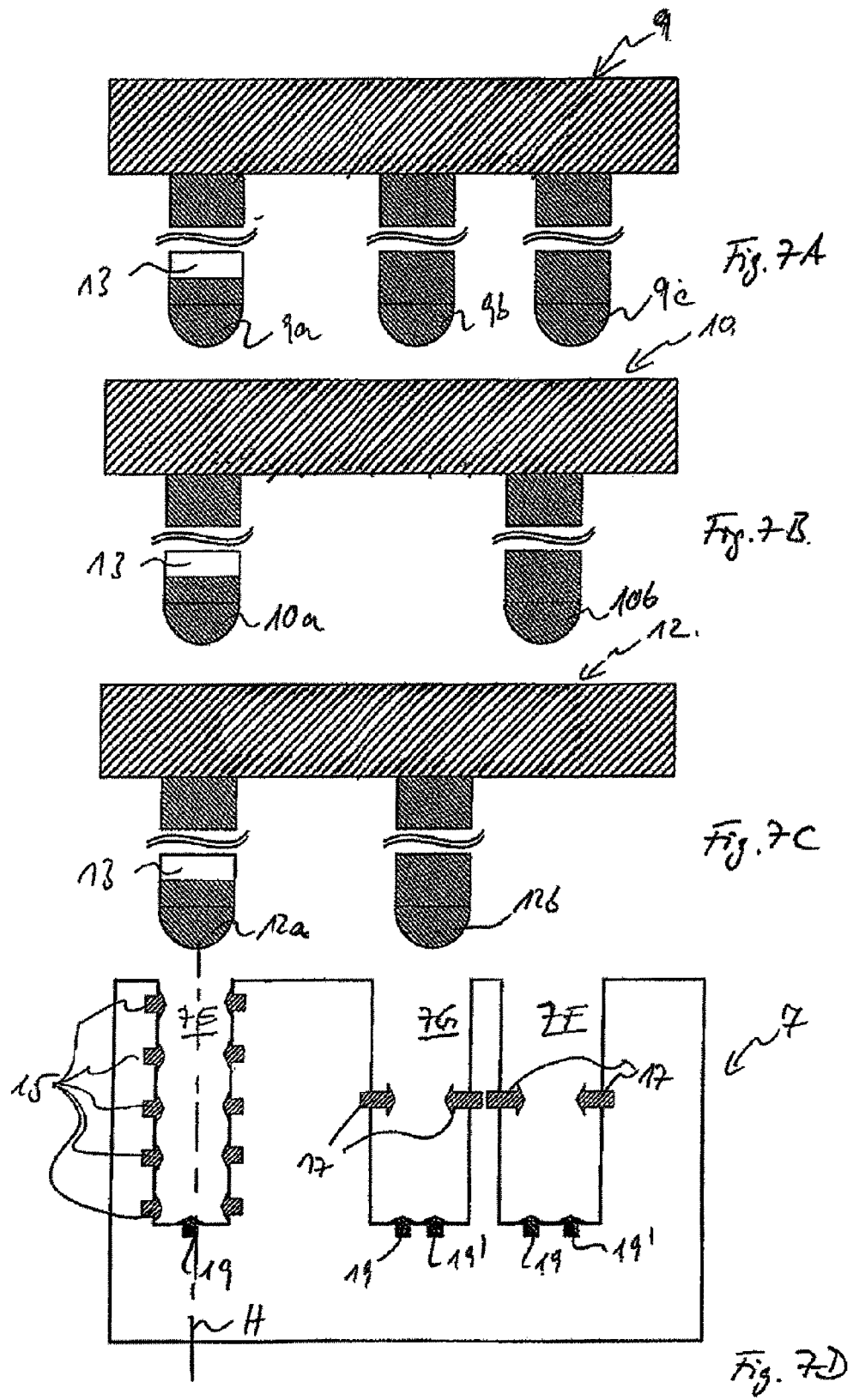

UNIVERSAL CONNECTOR SOCKET

CLAIM OF PRIORITY

This application claims priority to European patent application number EP 11 153 757.7, filed Feb. 9, 2011, the entirety of which is hereby incorporated by reference.

FIELD OF THE INVENTION

Embodiments of the present invention relate to a universal connector socket for a surgical apparatus.

BACKGROUND

Universal connector sockets are designed for installation in a surgical apparatus and for the connection of different plug connectors that can be associated with different electrosurgical instruments that are used in radio-frequency surgery. A universal connector socket has several plug contact openings that receive the contact pins of a respective plug connector, which can be connected to any electrosurgical instrument. An appropriate radio-frequency current is supplied to the electrosurgical instrument via the plug contact holes and the contact pins, in which case, an RF current is usually generated by an RF generator located in the surgical apparatus.

There have been many different plug and socket connectors for connecting accessories such as, for example, surgical handles or forceps to an RF surgical apparatus. Usually, these instruments are at most minimally different from each other regarding their function. However, the mechanical design of the associate plug and socket connectors can certainly vary. Indeed, each manufacturer of such equipment has its own design for plug and socket connectors in its product line, so that the plug and socket connectors of similar surgical instruments from different manufacturers may utilize connectors that are different from each other. As a result, different connector sockets are required for the connection of the same types of instruments. Over time, a few particularly advantageous types of plug connectors have been developed and offered by manufacturers.

There is a difference between strictly bipolar and strictly monopolar connector socket types, i.e., between connector sockets for connecting monopolar instruments comprising an active electrode and connector sockets for connecting bipolar instruments comprising two active electrodes. The monopolar "3-pin" plug connector, for example, represents a preferred monopolar plug connector type. As addressed hereinabove, this plug connector type can be used for accessories by third-party suppliers. Considering bipolar applications, two preferred plug connectors are available, each having two contact pins, whereby the contact pins of one plug connector are at a distance of 22 mm from each other and the contact pins of the other plug connector are at a distance of 28.5 mm from each other.

Universal connector sockets are available for a small range of plug and socket connectors that are able to accommodate various plug connectors; however, these are restricted to strictly bipolar or strictly monopolar applications. Also, regarding their functionality, these known connector sockets are greatly restricted. Usually, these are plug connectors that only exist as universal mechanical assemblies.

Therefore, it would be advantageous to provide a universal plug and socket connection and universal connector socket for a surgical apparatus. Such a plug and socket connection would advantageously feature improved mechanical universal usability and would also offer expanded functionality.

SUMMARY

The disclosed universal connector socket provides a universal plug and socket connection characterized in that, for selectively connecting monopolar and bipolar surgical instruments, several plug contact openings are arranged so as to overlap. Further, for holding an unambiguous plugging position of a plug connector, the disclosed universal connector socket provides a shared reference plug contact opening for different plug connectors, which is arranged separate from the other plug contact openings.

An aspect of the disclosed universal connector socket provides universal plug and socket connection that can accommodate monopolar as well as bipolar plug connectors that are common on the market and that respond in a functional manner to the inserted plug connector. To accomplish this, the plug and socket connection has at least one contact means in the form of an opening that is associated with the universal connector socket and at least one projecting contact element in the form of a projection, for example a pin, that is associated with the plug connector.

In addition, the shared reference contact opening provides an unambiguous plug connector position for different plug connectors, in which case the fixed relative distance of the contact elements of a plug connector ensures an unambiguous plug position. Consequently, a mechanical connector socket is suggested that has both round and oval and/or elongated plug contact openings to be able to cover the multitude of contact distances displayed by different plug connectors.

Preferably, at least one plug contact opening of the universal connector socket has several contact areas that are electrically separate from each other. Such contact areas can act as the connection with a contact element that also has several contact areas. When the contact element is plugged into the plug contact opening the contact areas of the contact element and of the plug contact opening contact each other and form electrically separated or insulated electric current paths and/or signal paths. The plurality of separate contact areas of the at least one plug contact opening can be configured and arranged in different ways.

For example, it is possible that the plug contact opening has, on its inside circumference, several contact areas that are electrically separated in an axial direction and is thus able to interact with a contact element in the manner of a lug jack. It is also possible that the plurality of contact areas of the at least one plug contact opening is arranged in longitudinal direction on its inside circumference. The contact areas can be electrically separate from each other and interact with a contact element whose contacts are also arranged electrically separate in a longitudinal direction.

The contact areas may be arranged over the entire length of a contact element or the corresponding plug contact opening. However, it is also possible for them to take up only a part of this length and be arranged sequentially in an electrically insulating manner or, in addition, next to each other on the circumference of the contact element or the plug contact opening.

It is also possible for a contact element to comprise several individual contact pins that are electrically insulated from each other. Then, the plug contact opening has a number of contact sockets corresponding to the number of contact pins in order to effectively ensure electrical contacting. The contact elements or contact pins may have a round, oval, square, rectangular or also a different form, in which case the plug contact opening allocated to the contact element or the contact pin has a corresponding cross-sectional form, so that an electrically operative connection is formed when the contact element and the plug contact opening are united. It is also possible that an electrical contacting between a plug contact opening and a contact element comprises a combination of differently configured contact areas, as described hereinabove.

Furthermore, the disclosed universal connector socket may comprise at least one plug detecting device so that a plug connector positioned in the universal connector socket can be detected. A plug detecting device may be implemented by at least one additional contact pin, by at least one Reed contact or by at least one microswitch. Furthermore, an instrument detecting device for detecting the surgical instrument type connected to the universal connector socket may be provided.

Preferably, at least two plug contact openings are provided in the universal connector socket, said contact openings having a distance of 22 mm from each other. Preferably, two additional plug contact openings are provided, said contact openings having a distance of 28.5 mm from each other. In this way, it is possible for the universal connector socket to accept bipolar plug connectors that have contact elements at different distances. Considering a particularly preferred embodiment, a total of five plug contact openings are provided along a common center axis.

BRIEF DESCRIPTION OF THE FIGURES

FIG. 5 shows a schematic representation of a multifunctional 3-pin plug connector for a monopolar electrosurgical instrument.

FIG. 6 shows a schematic representation of a simple 3-pin plug connector for a monopolar electrosurgical instrument.

FIG. 7A shows a schematic representation of a simple/multifunctional 3-pin plug connector for a monopolar electrosurgical instrument.

FIG. 7B shows a schematic representation of a first simple/multifunctional 2-pin plug connector for a bipolar electrosurgical instrument.

FIG. 7C shows a schematic representation of a second simple/multifunctional 2-pin plug connector for a bipolar electrosurgical instrument.

FIG. 7D shows a schematic sectional view of a universal connector socket in accordance with the invention.

DETAILED DESCRIPTION

Figure 1:
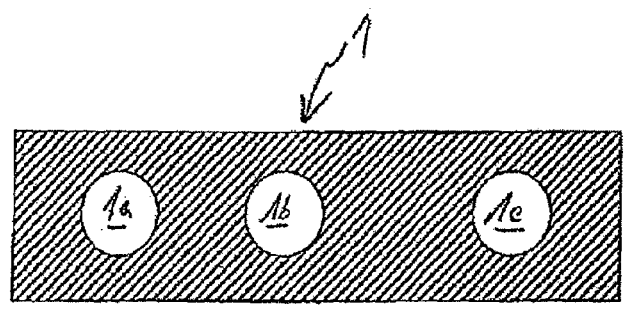
FIG. 1 shows a schematic plan view of a conventional 3-pin connector socket for the connection of a monopolar electrosurgical instrument.

Referring to the figures, wherein like reference numbers denote like features, FIG. 1 is a schematic plan view of a conventional 3-pin connector socket 1 for the connection of a monopolar electrosurgical instrument (the instrument not being shown in the figure). Here, the connector socket 1 is shown insulated; however, it is understood that, usually, the socket is an externally accessible integral part of a surgical apparatus. The connector socket 1 has a total of three plug contact openings 1a, 1b and 1c for receiving contact elements that—in this exemplary embodiment—are shown in the form of contact pins of a plug connector, in which case the plug connector may be connected with any surgical instrument. The depth of the plug contact openings preferably corresponds to the length of the contact elements, so that, preferably, the contact elements can be inserted all the way into the plug contact openings. An electrical connection between the plug contact openings and the contact elements is created via contacts that are provided on the inside wall of the plug contact openings and on the peripheral surface of the contact elements and that are in physical contact with each other when the contact elements are plugged into the plug contact openings. Via the electrical connection between the contacts of the plug contact openings 1a, 1b and the contact elements of the plug connector, the electrosurgical instrument is supplied with a radio-frequency current by the RF generator.

Figure 2:
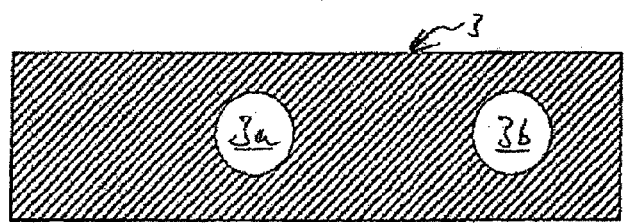
FIG. 2 shows a schematic plan view of a conventional 2-pin connector socket of a first type for the connection of a bipolar electrosurgical instrument.

FIG. 2 shows a conventional connector socket 3 for the connection of a bipolar surgical instrument. The socket has two plug contact openings 3a and 3b that are arranged at a distance of 22.0 mm from each other and are disposed to receive a corresponding plug connector. Consequently, a suitable plug connector has two matching contact elements that are also arranged at a distance of 22.0 mm from each other.

Figure 3:
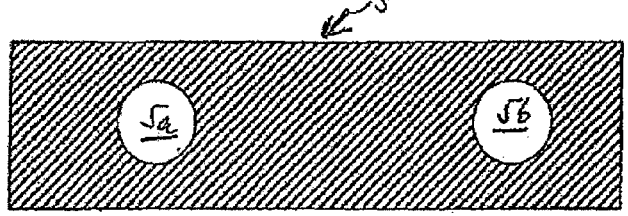
FIG. 3 shows a schematic plan view of a conventional 2-pin connector socket of a second type for the connection of a bipolar electrosurgical instrument.

FIG. 3 shows a third conventional connector socket 5 that is likewise disposed for the connection of a bipolar electrosurgical instrument. The connector socket 5 has two plug contact openings 5a and 5b that, in contrast with the connector socket 3 according to FIG. 2, are arranged at a distance of 28.5 mm from each other. The connector socket 5 is disposed to receive a corresponding plug connector that has two contact elements that are likewise arranged at a distance of 28.5 mm from each other.

The conventional connector sockets described hereinabove with reference to FIGS. 1-3 provide particularly preferred connector sockets that are offered by virtually every manufacturer of electromedical apparatuses or of electromedical accessories. Conventionally, the connector sockets are individually integrated in a surgical apparatus, so that, depending on the type of plug connector, a monopolar or a bipolar connector socket can be used for connecting an electrosurgical instrument.

Figure 4:
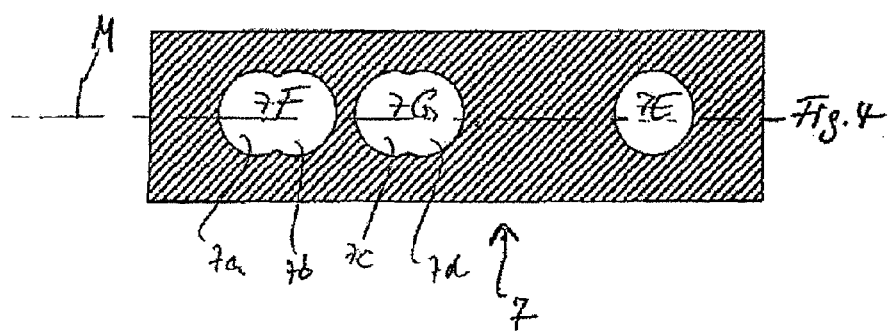
FIG. 4 shows a schematic plan view of a universal connector socket in accordance with the invention for the connection of a monopolar and a bipolar electrosurgical instrument.

FIG. 4 shows a schematic plan view of universal connector socket 7 in accordance with an embodiment of the invention. The universal connector socket 7 has the preferred monopolar and bipolar socket connectors (1, 3, 5 of FIGS. 1-3) in a single universal connector socket. Consequently, the universal connector socket 7 is disposed for the selective connection of monopolar and bipolar electrosurgical instruments. In contrast with conventional connector sockets, the universal connector socket has several plug contact openings 7a, 7b, 7c, 7d that are arranged—at least partially overlapping—along a center axis M of the universal connector socket 7. In addition, a circular plug contact opening 7E is provided and arranged separate from the other plug contact openings, i.e., not overlapping with any other plug contact opening.

Preferably, as shown by FIG. 4, respectively two of the plug contact openings, e.g., 7a and 7b or 7c and 7d, are arranged so as to overlap along the center axis M. Consequently, the plug contact openings can overlap in pairs. In this way, two of the plug contact openings 7a and 7b result in one essentially oval or elongated (extending along the center axis M) combined plug contact opening 7F, and the other two overlapping plug contact openings 7c and 7d also result in one combined, elongated or essentially oval plug contact opening 7G extending along the center axis M.

The plug contact openings 7a, 7b, 7c, 7d, as well as the separate plug contact opening 7E, are preferably arranged along the common center axis M of the universal connector socket 7. It is also possible to arrange at least a few of the plug contact openings 7a, 7b, 7c, 7d on concentric circles that have the plug contact opening 7E as their common center. However, considering the more space-saving and cost-favorable modification, the plug contact openings preferably overlap in pairs.

Referring to the present example, the position of the plug contact openings 7a, 7d and 7E and the distance between these plug contact openings correspond to the position and the distance between the plug contact openings 1a, 1b, 1c of the monopolar 3-pin connector socket of FIG. 1. Furthermore, the plug contact openings 7c and 7E are arranged such that their positions and distances from each other correspond to the plug contact openings 3a and 3b of the bipolar 22.0 mm 2-pin connector socket of FIG. 2. Finally, the plug contact openings 7b and 7E are arranged such that their positions and distances from each other correspond to the plug contact openings 5a and 5b of the bipolar 28.5 mm 2-pin connector socket of FIG. 2. It is understood that, for connecting plug connectors having distances between their contact elements different from the present examples, it is also possible to provide more than two overlapping plug contact openings or to have varying distances between the plug contact openings.

The plug contact opening 7E forms a shared reference contact opening for different plug connectors. This means that one of the contact elements of each plug connector that is connected to the universal connector socket can be always plugged into the reference plug contact opening. To accomplish this, the reference plug contact 7E is arranged separate from the remaining plug contact openings 7a, 7b, 7c and 7d or from the elongated plug contact openings 7F and 7G, e.g., not overlapping with another plug contact opening. Due to the matched distances between the contact elements of the plug connector and the plug contact openings of the universal connector socket, the correct plug position can provide for the additional contact element or the additional contact elements of the plug connector. In this manner, any additional plug position coding (keying), for example in the form of an asymmetry or a lug, is unnecessary.

The universal connector socket 7 shown at FIG. 4 is configured, due to the overlapping arrangement of plug contact openings and also due to the provision of a shared reference plug contact opening 7E, for different plug connectors such that said universal connector socket can receive plug connectors for both monopolar electrosurgical instruments and bipolar electrosurgical instruments.

FIG. 5 is a schematic side view of a plug connector 9 that is connected, via a connecting line 11, with an electrosurgical instrument (not shown in the Figure) for transmitting an RF current. For the connection with a connector socket, the plug connector 9 has three contact pins 9a, 9b and 9c and thus provides a connection between a surgical apparatus and a monopolar electrosurgical instrument. FIG. 1 shows an associated connector socket for use with the plug connector 9.

The plug connector 9 is configured as a multifunctional instrument plug. For this, the contact element 9a is provided with several electrically separate annular contact areas or contact surfaces 13 that are arranged in one axial direction along a center axis A of the contact element 9a in annular form at distances from each other on its peripheral surface. The contact surfaces 13 are connected to corresponding cables inside the contact element, said cables, in turn, leading to the electrosurgical instrument (not shown in the Figure) via the connecting line 11.

The annular contact surfaces 13 enable additional functionalities of the plug connector 9 or the electrosurgical instrument such as, for example, instrument detection or activation detection, as will be explained hereinafter.

FIG. 6 shows a plug connector 9' that also has three contact elements 9a', 9b' and 9c' and that is also connected—via a connecting cable 11'—with a corresponding monopolar electrosurgical instrument. However, in contrast with the plug connector 9 as in FIG. 5, plug connector 9' is not configured as a multifunctional plug connector and thus does not allow additional functions. Consequently, contact element 9a' does not form any annular, electrically separate contact surfaces but has a single continuous contact surface 14 that is plugged into a corresponding plug connector opening of the connector socket.

FIGS. 7A-7C show various exemplary plug connector types that can be plugged into an universal connector socket in accordance with the device shown in FIG. 7D. In so doing, the shown positions of the plug connectors in FIGS. 7B-7C correspond to the correct plug-in positions of the universal connector socket in accordance with the device shown in FIG. 7D.

FIG. 7A shows the plug connector 9 that may either be configured simply with a single contact surface or multifunctionally with several contact surfaces 13 on at least one contact element. Likewise, the plug connectors 10 and 12 having two contact elements 10a and 10b or 12a and 12b in accordance with FIGS. 7B and 7C can either be configured "simply" with a single contact surface or multifunctionally with several contact surfaces on at least one contact element. FIGS. 7A through 7C illustrate that, in the present example, the plurality of annular contact surfaces 13 are preferably provided on the contact element 9a, 10a and 12a that is inserted in the reference plug contact opening 7E ("reference contact pin"). It is understood that it is also possible to arrange the plurality of contact surfaces 13 on any other contact element or also on several contact elements.

FIG. 7D illustrates that the elongated plug contact openings 7F and 7G, these having two overlapping conventional plug contact openings, provide the option of connecting plug connectors for monopolar surgical instruments as well as for bipolar surgical instruments to the universal connector socket 7.

FIG. 7D shows the reference plug contact opening 7E configured for receiving a multifunctional plug connector, e.g., for receiving a plug connector having at least one contact element with several contact areas 13. For this, at least the reference plug contact opening 7E has, on its inside, several contact areas 15 that are preferably annular and are arranged along a center axis H of the reference plug contact opening 7E in axial direction electrically separate from each other in the wall region of the reference plug contact opening 7E and that, in plugged in state of a multifunctional plug connector such as, for example, the plug connector 9 of FIG. 5 come into contact with the contact areas 13 of the contact element 9a. The contact areas 15 are connected with lines that form separate electric current paths and/or signal paths. Via the lines, the contact areas 15 can be connected, for example with a switching matrix and/or a control device of the surgical apparatus.

As a result of the plurality of contact areas 15 in the plug contact opening 7E it is possible for the plurality of contact areas 13 on the contact element 9a to be contacted to implement an expanded functionality, for example, an instrument detection or an activation detection of the surgical instrument. If a standard instrument without a multifunction plug connector having a single contact per contact element is plugged into the socket, the plurality of contact areas 15 in the plug contact opening are short-circuited at least in part, and the surgical instrument can be used, as is customary, without the expanded functionality.

FIG. 7D additionally shows that the plug contact openings 7F and 7G can also have contact surfaces or contact areas 17 that are disposed to contact respectively one of the contact elements of the plug connectors. The contact areas 17 of the shared plug contact openings 7F and 7G are preferably arranged in an annular form along the inside surface of the plug contact openings. However, it is also possible to provide separate contact areas for each individual plug contact opening 7a, 7b, 7c and 7d so that at least two contact areas can be provided for each shared plug contact opening 7F and 7G, respectively.

In addition, the sectional view of the inventive universal connector socket in accordance with FIG. 7D shows that the plug contact openings 7F and 7G have—due to the overlapping arrangement of respectively two plug contact openings—a cross-section with an inside width that is greater in the direction of the center axis M than the width of a single plug contact opening and, in particular, greater than the reference plug contact opening 7E. In this way, it is possible to selectively insert the contact elements 10b as well as 9c in the plug contact opening 7F and the contact elements 12b and 9b in the plug contact opening 7G.

In addition to the mechanical compatibility with numerous plug connectors that are common on the market it is also possible to integrate a device into the disclosed universal connector socket that allows the detection of the presence of the individual contact elements of the plug connectors when plugged into the plug contact openings. For this, one or more plug detecting devices 19 and 19' can be provided in particular at the bottom of the plug contact openings or also in any other suitable position in or on the plug contact openings. In order to prevent that an RF signal is output to a contact area that is not intended therefor, an unambiguous allocation of the existing contact areas to one type of instrument should be ensured. This can be achieved by an electrical or electromechanical device such as, for example, additional contact elements, microswitches or a Reed contact, etc.

In the operating mode of the surgical apparatus, the functionality of the universal connector socket may be as follows. The plug detecting device 19 or 19' outputs feedback, e.g., in the form of a signal, about the "plug-in status" of the universal connector socket to a control device of the RF surgical apparatus, e.g., in particular that a plug connector is connected to the universal connector socket and, preferably, also what electrosurgical instrument is connected to the plug connector (monopolar, bipolar, instrument type, activation status, etc.). For example, if the contact element 12b of the plug connecter 12 is detected in the plug contact opening 7G by the plug detecting device 19', feedback is provided to the control device indicating that a two-pin bipolar plug connector (22.0 mm) is connected to the universal connector socket 7, whereupon an appropriate electric current is output by the RF generator to the electrosurgical instrument. To the extent that instrument detection can be implemented, in particular, by the multifunctional configuration of a plug contact opening 7E having several contact areas 15 and corresponding contact areas 13 of a contact element 12a, an exact adaptation of the electric current parameters to a specific electrosurgical instrument is possible.

After the feedback has been received by the plug detecting device, the control device of the surgical apparatus generates a signal that—consistent with the feedback regarding the contact configuration—ensures that an RF current is enabled to the matching contact elements in the plug contact openings. Depending on the instrument, it is possible to use individual contact elements for the output of the RF current as well as a signal line, for example for an activation detection. In multifunctional instruments, the detection of the instrument type can be implemented via electrical signals, for example, by a resistor, an EEPROM or a microcontroller in the instrument, by way of the additional annular contact surfaces that are separated from each other in axial direction.

In the present example, the multifunctional contact elements, i.e., the contact pins having several contact surfaces or contact areas that are separated from each other in an axial direction, are configured in the way of a lug jack. However, it is also possible that the contact element having several contact surfaces has several electrically separated contact pins that extend in one axial direction parallel to each other. It is understood that, in this case, the associated plug contact opening has corresponding, electrically separated contact opening areas or contact sockets for receiving the contact pins, by way of which a multifunctional actuation of the individually connected electrosurgical instrument is then possible.

The universal connector socket 7 in accordance with this embodiment of the invention can be connected to monopolar and bipolar plug connectors that are common on the market and also that a reference contact opening 7E pre-specifying an unambiguous plug-in position for a plug connector is provided. The reference contact opening 7E in connection with the pre-specified distances of the contact elements ensures correct positioning of the plug connector in the universal connector socket. As a result of the fixed contact distances of the pins from each other in the case of each plug connector or plug, an unambiguous plug position is thus guaranteed. It is understood that, in addition, the detection of the single plug-in option can be implemented in that a reference contact having a specific form or a mechanical code (key) is provided such as, for example an asymmetry or a lug. The electronic solution may be a switching matrix, a control, a preselection device or a data memory. Inasmuch as each plug system may have a different contact assignment, the surgical apparatus should be able to adjust the contact assignment on the universal connector socket to the currently plugged-in plug connector, e.g., a plug detection and an allocation of the plug are necessary.

To the extent that an additional functionality of a multi-functional plug connector can be implemented via a contact element or a plug contact opening, the plug connector may preferably have up to 8 or more contact elements in the form of contact pins.

The connector socket in accordance with the invention may also have additional other contact elements or contact means for the transmission of electrical signals or data. These contact means may be in the form of a universal serial bus (USB) contact, for example.

A universal connector socket 7 for a surgical apparatus is suggested for the connection of different plug connectors 9, 9', 10, 12 of different surgical instruments for RF surgery. The universal connector socket preferably has several plug contact openings 7a, 7b, 7c, 7d, 7E for receiving the contact elements 9a, 9a', 9b, 9b', 9c, 9c', 10a, 10b, 12a, 12b of a plug connector 9, 9', 10, 12. The universal connector socket 7 is characterized in that, for selectively connecting monopolar and bipolar surgical instruments, several plug contact openings 7a, 7b, 7c, 7d are arranged in an overlapping manner, and that, for defining an unambiguous plug-in position of a plug connector 9, 9', 10, 12, a shared reference plug contact opening 7E for different plug connectors is provided. Such a reference plug contact opening can be arranged separate from the other plug contact openings 7a, 7b, 7c, 7d.

A number of embodiments have been described. Nevertheless, it will be understood that various modifications may be made thereto without departing from the scope of the invention. It should also be understood that the appended drawings are not necessarily to scale, presenting a somewhat simplified representation of various preferred features illustrative of the basic principles of the invention. The invention should not be limited to any particular embodiment or feature disclosed, but is defined by the appended claims.

What is claimed is:

1. A universal connector socket for a surgical apparatus for the connection of plug connectors of surgical instruments for radio-frequency surgery and having several plug contact openings for receiving contact elements of a plug connector, comprising:
   a plurality of plug contact openings arranged in an at least partially overlapping manner for selectively connecting monopolar surgical instruments and bipolar surgical instruments, the plurality of plug contact openings defining an unambiguous plug-in position for a plug connector; and
   a shared reference plug contact opening for different plug connectors, wherein the shared reference plug contact opening is arranged separate from the plurality of plug contact openings.

2. The universal connector socket of claim 1, wherein at least one of the plurality of plug contact openings has a plurality of electrically separate contact areas for contacting a contact element.

3. The universal connector socket of claim 2, wherein the plurality of electrically separate contact areas are configured for contacting a contact element configured in the manner of a lug jack and having a plurality of electrically separate contact areas arranged in an axial direction of the contact element.

4. The universal connector socket of claim 1, further comprising at least one plug detecting device for detecting a plug connector present in the universal connector socket.

5. The universal connector socket of claim 4, wherein the at least one plug detecting device comprises at least one additional contact pin, at least one Reed contact, or at least one microswitch.

6. The universal connector socket of claim 1, further comprising an instrument detecting device for detecting the type of surgical instrument connected to the universal connector socket.

7. The universal connector socket of claim 1, wherein at least two plug contact openings of the plurality of plug contact openings are provided at a distance of 22.0 mm from each other.

8. The universal connector socket of claim 1, wherein at least two plug contact openings of the plurality of plug contact openings are provided at a distance of 28.5 mm from each other.

9. The universal connector socket of claim 1, wherein a cross-section of a plug contact opening formed of two overlapping plug contact openings of the plurality of plug contact openings is different from a cross-section of the shared reference plug contact opening.

10. The universal connector socket of claim 9, wherein a width of the cross-section of a plug contact opening formed of two overlapping plug contact openings of the plurality of plug contact openings measured in longitudinal direction of the center axis the universal connector socket is greater than the width of the cross-section of the shared reference plug contact opening.

11. A plug and socket connection, comprising:
   at least one plug connector that has at least two contact elements; and
   an universal connector socket, comprising:
      a plurality of plug contact openings arranged in an at least partially overlapping manner for selectively connecting monopolar surgical instruments and bipolar surgical instruments, the plurality of plug contact openings defining an unambiguous plug-in position for the at least one plug connector; and
      a shared reference plug contact opening for different plug connectors, wherein the shared reference plug contact opening is arranged separate from the plurality of plug contact openings.

12. The plug and socket connection of claim 11, further comprising at least one contact comprising a contact pin and at least one additional contact comprising a socket, wherein the contact pin and the contact socket comprise a plurality of electrically separate contact areas, wherein the contact socket is allocated to the plug contact opening and the contact pin is allocated to the contact element.

* * * * *